United States Patent
Mahajan et al.

(10) Patent No.: US 7,398,669 B2
(45) Date of Patent: Jul. 15, 2008

(54) TEST APPARATUS AND METHOD OF MEASURING SURFACE FRICTION OF A BRAKE PAD INSULATOR MATERIAL AND METHOD OF USE OF A BRAKE DYNAMOMETER

(75) Inventors: Sanjay K. Mahajan, Farmington Hills, MI (US); Eric Denys, Ann Arbor, MI (US)

(73) Assignee: Material Sciences Corporation, Elk Grove, IL (US)

( * ) Notice: Subject to any disclaimer, the term of this patent is extended or adjusted under 35 U.S.C. 154(b) by 332 days.

(21) Appl. No.: 11/236,940

(22) Filed: Sep. 28, 2005

(65) Prior Publication Data

US 2007/0068220 A1    Mar. 29, 2007

(51) Int. Cl.
*G01N 3/56* (2006.01)

(52) U.S. Cl. .................................. 73/10; 73/9
(58) Field of Classification Search ................ None
See application file for complete search history.

(56) References Cited

U.S. PATENT DOCUMENTS

| | | | |
|---|---|---|---|
| 3,717,025 A * | 2/1973 | Kronenberg et al. ............. 73/9 |
| 4,109,519 A | 8/1978 | Bartlett et al. |
| 5,689,058 A * | 11/1997 | Yuan ................................. 73/9 |
| 6,557,889 B2 * | 5/2003 | Breed ........................... 280/735 |
| 6,644,094 B1 | 11/2003 | Otaki et al. |
| 6,691,551 B2 | 2/2004 | Otaki et al. |
| 6,752,001 B1 * | 6/2004 | LaPointe ........................ 73/10 |
| 6,843,128 B2 | 1/2005 | Chen et al. |
| 2002/0189910 A1 * | 12/2002 | Yano et al. ................ 188/73.37 |
| 2004/0107772 A1 * | 6/2004 | Chen et al. ..................... 73/574 |

* cited by examiner

*Primary Examiner*—Robert R Raevis
(74) *Attorney, Agent, or Firm*—Quinn Law Group, PLLC; Christopher W. Quinn; Jean M. McCarthy

(57) ABSTRACT

A test apparatus for measuring surface friction of a damping material such as brake pad insulator material includes a rotor configured to support the damping material for rotation therewith, an actuator pressurizable to apply axially-inward force to the damping material and a stator configured to support the actuator. A sensor determines the force applied to the actuator and a torque cell is axially aligned with the rotor for measuring torque of the rotor in relation to force applied to the damping material. The calculation of surface friction of the damping material is possible based on the measured load and torque. A method of measuring surface friction of a brake pad insulator material as well as a method using a brake dynamometer is also presented.

14 Claims, 2 Drawing Sheets

TEST APPARATUS AND METHOD OF MEASURING SURFACE FRICTION OF A BRAKE PAD INSULATOR MATERIAL AND METHOD OF USE OF A BRAKE DYNAMOMETER

TECHNICAL FIELD

This application relates to an apparatus for testing damping material and specifically a method of measuring surface friction of automotive brake pad insulator material.

BACKGROUND OF THE INVENTION

Brake pad insulators are typically used on the backing plate of a disk brake. Brake pad insulators are designed to perform a damping function at various vibrations, frequencies and temperatures. The brake pad insulators thus help quiet vibrations and induced noise of the disk brake pad.

Brake pad insulators exploit various damping mechanisms to achieve the desired noise reduction. It is hypothesized that insulators attenuate noise by extensional damping, shear-deformation, isolation damping and frictional damping. Extensional damping may also be referred to as free layer damping and involves relative movement of a relatively soft layer of material that is over, on or otherwise connected with a relatively stiff layer of material. If the stiff layer bends the soft layer stretches but does not shear. Shear-deformation damping, also referred to as constrained damping, involves relative movement of a soft layer of material positioned between two stiff layers. The stiff layers act as constraints and shear occurs in the soft material but mostly only bending occurs in the stiffer material. Isolation damping is well understood to be the type of damping occurring when the insulator absorbs vibration pulses. For instance, vibrations between the brake pad and rotor may be damped by axial compression of the insulator.

Frictional damping is perhaps the least studied of the damping mechanisms occurring with a brake pad insulator. Frictional damping occurs between contacting surfaces that have relative slip. In the brake pad insulator example, the outermost layer of the brake pad insulator is contacted by a brake actuator such as a piston or a caliper finger. Relative slip may occur, resulting in surface friction damping.

There are many mathematical models that can be construed to represent frictional forces between contacting surfaces. The simplest and fundamental representation shown below, is the Coulomb friction model, which relates the total frictional (damping) force ($F_f$) between contacting bodies, to the net contact force ($F_c$), through the kinetic coefficient of friction $\mu_k$. The direction of the frictional force depends upon the sign (sgn) of the relative velocity (v) between contacting surfaces. The value of sgn(v) is +1 or −1.

$$F_f = \mu_k \cdot F_c \cdot sgn(v)$$

The values of friction measured near zero relative velocities (i.e., at the transition from sticking contact to slipping contact,) lead to the static coefficient of friction, $\mu$, which itself is usually a good indicator of the surface frictional damping that can occur between contacting and slipping surfaces. Therefore, frictional damping of a brake pad insulator can be quantified by determining the surface friction. Known methods of surface friction measurements are not suitable for brake pad insulator material. For example, the American Society for Testing and Materials (ASTM) Standard D 1894-01 is a standard method for determining the static and kinetic coefficients of friction of film and sheeting. The test method determines the coefficients of starting and sliding plastic film and sheeting when sliding over itself or other substances at specified test conditions. The procedure permits the use of a stationary sled with a moving plane, or a moving sled with a stationary plane. The sled and plane maybe referred to as a "sliding table" design. ASTM D 1894-01 standard method uses a pressure of less than one bar which makes the test unsuitable for measuring surface friction of brake pad insulators under realistic conditions, since the operating pressures in disk brakes are much higher, i.e., on the order of 10 times higher. Applying the method to a brake pad insulator would require a more rigid and frictionless sliding table. Also, it is cumbersome to test at temperatures other than ambient under ASTM D 1894-01, as the plane may be seated while the sled must be held at the ambient temperature. Finally, the ATSM D 1894-01 method is based on linear sliding instead of rotary, and is therefore not representative of a brake pad insulator application.

Known friction measurement test rigs for brake linings (i.e., brake pads) are relatively bulky and have high rigidity requirements due to the relatively large rotational displacement requirements and torque existing between a brake pad and a rotor. Insulators operate under conditions of much smaller relative motion (i.e., the movement between the insulator and the actuating brake piston or brake caliper finger) or load, making these friction measurements test rigs not quite suitable for brake pad insulator friction measurement.

It is desirable to know the surface friction characteristics of a damping material, such as brake pad insulator material, under specific conditions, such as likely in-use conditions including the ranges of temperatures, pressures and torques that the insulators will be subjected to, in order to evaluate the effect of surface friction on overall damping capability.

SUMMARY OF THE INVENTION

A test apparatus for measuring surface friction of the damping material is provided that allows relatively easy testing and measurement of friction in known (i.e., controlled) conditions. Measuring of the coefficient of friction under typical or other specifically controlled loading and temperature conditions is possible. The test apparatus allows determination of the frictional damping mechanism of a brake pad insulator, which has not heretofore been accomplished, possibly due to the unsuitability of known tests, as discussed above.

The test apparatus includes a rotor configured to operatively support the damping material for rotation therewith. A stator is configured to operatively support at least one actuator that is operable (i.e., pressurizable) to apply axially-inward force on the damping material. A torque cell is mounted on the rotor for measuring torque of the rotor in relation to pressure applied to the damping material by the actuator. A calculation of surface friction of the damping material may be made according to the following formula for the coefficient of effective static friction:

$$\mu^1 = \frac{T^1_{BA}/r_{eff}}{F^1_N}$$

where, the superscript 1 refers to a first sample of damping material. In the above formula, $T^1_{BA}$ is the portion of the measured break-away torque acting on the first sample, $r_{eff}$ is the effective radius where friction is evaluated, and $F^1_N$ is the net normal (axially-inward) force acting on the first sample at contact.

The test apparatus allows for easy and efficient testing of multiple samples of damping material at the same time and, if desired, different types of damping materials. Because the rotor is configured like a typical brake rotor having first outer surface and a second outer surface opposing the first outer surface, the first and a second sample of, preferably, the same insulator damping material may be outwardly supported at the respective outer surfaces. A brake piston and a caliper finger coupon (or, alternatively, two brake pistons; or, two caliper finger coupons) connected thereto act as first and second actuators employed to apply opposing axially-inward forces to the samples via the opposing piston and finger. A caliper finger "coupon" is a sample or section of a caliper finger that is used in a brake assembly employing the damping method. The first actuator applies an axially-inward force on the first sample and the second actuator applies an axially inward force on the second sample. More than one sample may also be tested on either the first or second outer surfaces of the rotor (i.e., on the same side of the rotor). The opposing axially-inward forces applied to the respective damping material samples are both toward the rotor and cancel one another so that the rotor is not loaded along its axis, reducing the need for a highly rigid support structure.

Preferably, carrier members are supported within recesses formed or machined in the rotor. The carrier members are supported for common rotation with the rotor and are operable for supporting the samples of the damping material. The recesses are spaced from one another either on the same side of the rotor or on different sides of the rotor (i.e., on the same or on both of the first outer surface and the second outer surface). The recesses permit multiple samples or types of materials to be tested under the same loading and temperature conditions.

A temperature sensor may be operatively connected with the damping material for sensing the temperature thereof so that the coefficient of friction maybe correlated with temperature. A heater element may be operatively associated with the damping material for varying the temperature thereof. Alternatively, the entire test apparatus may be placed in a controlled temperature environment, such as a test chamber or shed.

The test apparatus may be used to test brake pad insulator material (i.e., the damping material may be brake pad insulator material) using actual brake pistons and brake finger coupons designed for a specific brake application so that actual in-use conditions may be more closely replicated. However, the test apparatus is not limited to testing of brake pad insulator materials. The damping material studied may likewise be any other material used in an application where friction between mating surfaces as a function of pressure, surface area and temperature is required.

As may be apparent from the description of the test apparatus described above, a method of measuring surface friction of a brake pad insulator material is provided. The method includes operatively connecting the brake pad insulator material to a rotor for rotation therewith. The method includes applying an axially-inward force on the brake pad insulator material, measuring the axial force and powering the rotor for rotation. Finally, the method includes measuring torque on the rotor, thereby allowing a calculation of surface friction of the brake pad insulator material based on the measured axial force and torque.

Preferably, the method includes varying the temperature of the brake pad insulator material so that a correlation of the calculated surface friction with temperature may be made.

The method may include creating a recess in the rotor and securing a carrier member at least partially within the recess for rotation with the rotor. The brake pad insulator material is then connected to the carrier member. Multiple recesses may be created so that multiple samples of brake pad insulator material, either of the same type of material or different types, may be tested at multiple carrier members supported within the recesses on the rotor. Repeated use of the carrier members from test to test is made simple by removing the brake pad insulator material from each carrier member and connecting (e.g., bonding) the second sample of brake pad insulator material to the carrier member and then repeating the steps of applying an axial force, measuring the axial force, powering the rotor and measuring torque to the rotor. Thus, calculation of surface friction of the second sample of brake pad insulator material is possible.

The test apparatus is well suited for use on a brake dynamometer. Specifically, the test apparatus has a configuration similar to a brake system (such as having a rotor, a stator and an actuator), which allows the use of a brake dynamometer so the appropriate loading may be applied and acquisition of relevant quantities can be carried out easily to evaluate friction between actual surfaces used in the brake system (i.e., using the actual brake pistons and fingers that will contact the brake pad insulator material). The existing controller (governing actuation, data acquisition and test automation) of the brake dynamometer is employed. Accordingly, a method of using a brake dynamometer includes providing a rotor, a stator, at least one actuator and damping material. The method includes operatively connecting the rotor with a rotatable shaft of the brake dynamometer for common rotation therewith. The method further includes grounding the stator and operatively connecting the actuator to the stator and to a controller on the brake dynamometer. Next, the damping material is operatively connected to the rotor and force is applied to the damping material via the actuator. The method includes rotating the rotor while the force is being applied and measuring torque on the rotor, thereby allowing calculation of surface friction of the damping material.

As discussed above with respect to the test apparatus and the method of measuring surface friction, recesses may be formed in the rotor to support carrier members to which the damping material is connected. Actuators, such as a brake piston and a caliper finger coupon may be utilized so that the applied force step includes applying force to a first side of the rotor at a first damping material sample and applying second force via the finger coupon to an opposing side of the rotor at the second sample with the applied forces being axially opposed so that no net force is applied to the rotor.

The method of using a brake dynamometer may include controlling the temperature of the damping material via a heating element or, alternatively, by placing the test apparatus in a controlled ambient environment. Since brake dynamometers typically are equipped with an existing torque cell appropriate for measuring higher levels of torque than will exist between the typical piston or finger actuator and damping material, it may be desirable to replace the existing torque cell with a replacement torque cell calibrated to measure relatively lower levels torque.

The above features and advantages and other features and advantages of the present invention are readily apparent from the following detailed description of the best mode for carrying out the invention when taken in connection with the accompanying drawings.

DESCRIPTION OF THE PREFERRED EMBODIMENT

Figure 1:
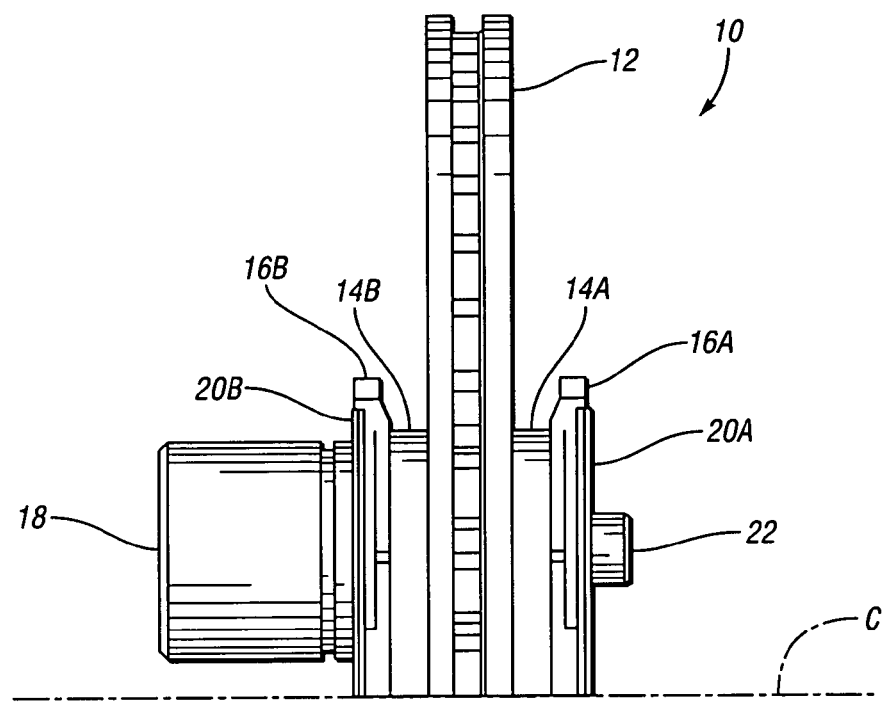
FIG. 1 is a fragmentary schematic side view illustration of a disk brake assembly utilizing brake pad insulator material.

Referring to the drawings, wherein like reference numbers refer to like components, FIG. 1 shows a typical automotive disk brake assembly 10. The disc brake assembly 10 includes a disk rotor 12 rotating about a center line C. The rotor 12 will be operatively connected to a wheel that also rotates about center line C, as is well understood by those skilled in the art. An inner disk brake pad 14A and an outer disk brake pad 14B are axially moveable via brake piston 18 into contact with the disk rotor 12 for braking the rotor 12 and, thereby, the wheel. Each of the brake pads 14A, 14B is of a selected frictional material. Each brake pad 14A, 14B has a respective metal backing plate 16A, 16B adhered or otherwise connected to it outward of the brake disk rotor 12. Brake pad insulator material 20A, 20B, also referred to herein as damping material, is applied to the outer side of each respective of the backing plates 16A, 16B. The brake pad insulator material 20A, 20B may be multi-layered, having relatively stiff and soft layers. Fluid pressure from a fluid source on the vehicle is applied when the operator steps on the brake pedal to force the brake piston 18 axially-inward into contact with the brake pad insulator material 20B and the brake pad 14B into contact with the disk rotor 12. A brake caliper finger 22 is operatively connected with the piston 18 and is also forced axially-inward into contact with brake pad insulator material 20A when fluid pressure is applied to the brake piston 18, as will be well understood by those skilled in the art. The piston 18, caliper finger 22, brake pad insulator 20A and 20B, backing plate 16A and 16B and brake pads 14A, 14B do not rotate with the disk rotor 12 but move axially with respect thereto. A typical brake caliper may extend between the piston 18 and the caliper finger 22, as will be readily understood by those skilled in the art. As discussed above, various damping mechanisms occur in the brake pad insulator material 20A, 20B, including frictional damping due to relative movement between the piston 18 and the brake pad insulator material 20B and between the caliper finger 22 and the brake pad insulator material 20A. Quantification of the coefficient of friction of the brake pad insulator material 20A and 20B during braking under various operating conditions, including forces applied by the piston 18 and caliper finger 22, temperature of the brake pad insulator material 20A and 20B and torque of the disk rotor 12 during braking, is an important quantity to be determined in understanding damping capabilities. The brake piston 18 maybe referred to as a first actuator and the brake caliper finger 22 maybe referred to herein as a second actuator.

Figure 2:
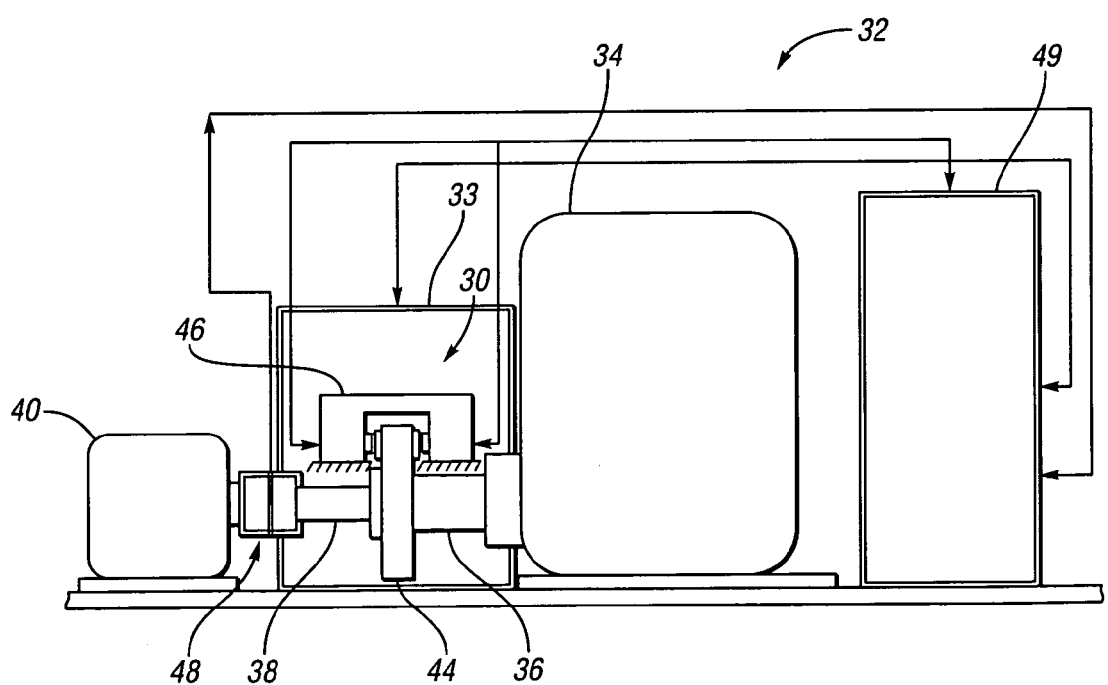
FIG. 2 is a schematic illustration of a test apparatus operatively connected to a brake dynamometer for measuring surface friction of the brake pad insulator material of FIG. 1.

Referring now to FIG. 2, the test apparatus 30 is connected with a brake dynamometer 32 for determining surface friction of brake pad insulator materials 20A and 20B of FIG. 1. The brake dynamometer 32 includes a motor housed within motor housing 34 which drives a rotatable shaft 36. The dynamometer 32 further includes a power transfer axle 38 grounded to a load bearing member 40 which holds the power transfer axle 38 stationary. The motor housing 34 and the load bearing member 40 are grounded.

The test apparatus 30 includes a rotor 44 (which may also be referred to as a rotor fixture) connected for rotation with the rotatable shaft 36. The test apparatus 30 also includes a stator 46 (which may also be referred to as stator fixture). The stator 46 is grounded. The stator 46 may be grounded either independently from the dynamometer 32 (e.g., via support legs running to the ground) or may be grounded via the stationary power transfer shaft 38. For instance, a hub may extend from the left side of the stator 46 and be supported on the stationary transfer shaft 38.

The test apparatus 30 also includes a torque measurement cell 48 which functions to measure torque of the rotor 44 when braked, the torque being conveyed through the power transfer shaft 38. The measured torque is relayed to the dynamometer controller. The test apparatus 30 further includes opposing actuators, preferably the piston 18 and the caliper finger 22 of FIG. 1, to apply force via hydraulic pressure controlled by the controller 49 to brake pad insulator material 20A, 20B. The brake pad insulator material 20A, 20B is supported on the rotor 44. The pressure applied is recorded by the controller 49. As will be well understood by those skilled in the art, typically a preassembled brake disk assembly such as the brake disk assembly 10 of FIG. 1 is supported by the brake dynamometer 32 to test functioning of the brake pads 14A, 14B, the piston 18 and the caliper finger 22 in braking the rotor 12. The brake dynamometer 32 is used herein, however, to support the test apparatus 30 for measuring the coefficient of friction of the brake pad insulator material 20A, 20B. Because the test apparatus 30 has a brake-like configuration (i.e., includes a rotor 44 and an actuator) the brake dynamometer 32 is easily modified for use with the test apparatus 30. The test apparatus 30 may be housed within an environmental chamber or shed 33, the temperature of which is controlled and recorded by the controller 49, to thereby control the temperature of the brake pad insulator material 20A, 20B (shown in FIG. 4) supported by the rotor 44. Alternatively, temperature of the brake pad insulator material may be controlled by a heater element and a thermocouple connected thereto, as shown and described with respect to FIG. 4.

Figure 3:
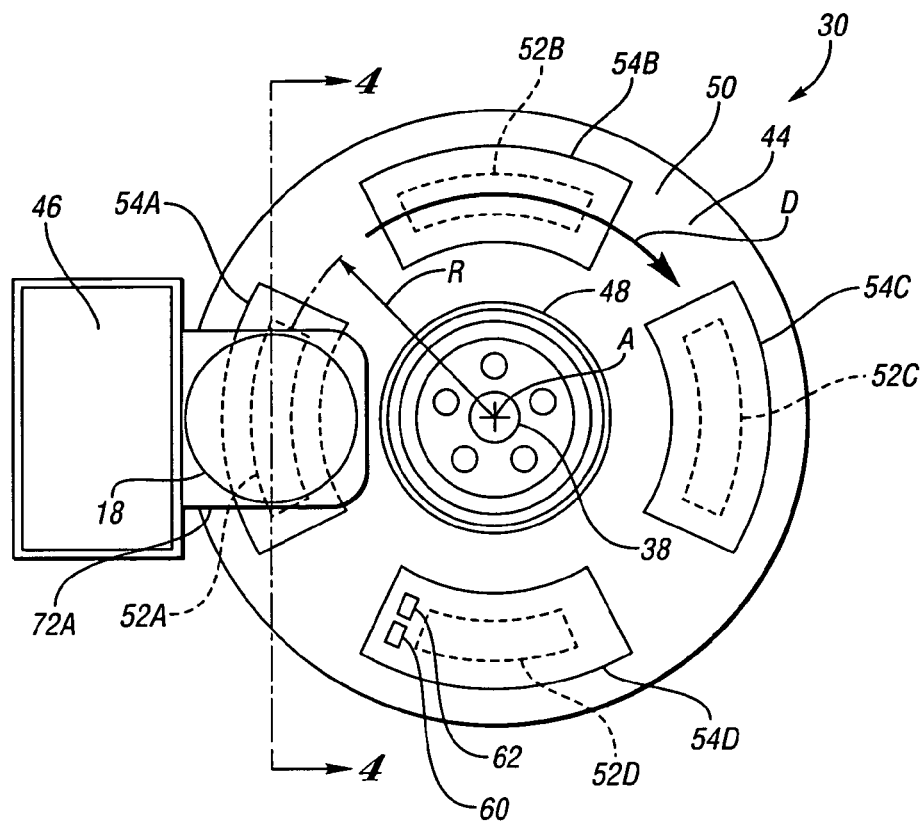
FIG. 3 is a schematic side view illustration of the test apparatus of FIG. 2.

Referring to FIG. 3, the test apparatus 30 is shown with a first outer surface 50 of the rotor 44 formed with recesses 52A, 52B, 52C and 52D. Within the scope of the invention, only one of the recesses may be formed on the outer surface 44 or additional recesses beyond those illustrated may be formed. A different carrier member 54A, 54B, 54C, 54D is inserted in each of the respective recesses 52A-52D so that the carrier members are supported by the rotor 44. The carrier members 54A-54D may be adhered, bonded, fastened or connected to the rotor 44 in any way known to those skilled in the art so that the carrier members 54A-54D rotate with the rotor. A sample of damping material is supported at each respective one of the carrier members 54A-54D, as will be best illustrated in FIG. 4. The samples preferably include the brake pad insulator material 20A, 20B of FIG. 1. The stator 46 supports the piston 18 which is in fluid communication with the controller 49 of the dynamometer 32 of FIG. 2 to apply a force to the brake pad insulator material carried on the rotor 44, the force being in a direction parallel with an axis of rotation A through the center of the test apparatus 30. The torque cell 48 is shown axially aligned with the rotor 44 and carried on the power transfer shaft 38 to measure a "breakaway" torque of the rotor 44, that is, the torque required to cause rotation of the rotor 44 under the load applied by the piston 18 (and by the finger 22). Fluid pressure applied to the piston 18, may be used to determine the axial force applied to the brake pad insulator supported on the carrier members 54A-54D (under the well known relationship:

$$F = P \times A;$$

where, F is force in Newtons, P is pressure in N/m² and A is effective area of the contact of the piston 18 on the brake pad insulator material 20B). A heater element 60 and a temperature sensor 62 may be installed within each insulator carrier, as shown only on insulator carrier 54D, but as may exist on each of the insulator carriers. The heater element 60 and temperature sensor 62 may be operatively connected to the controller 49 of FIG. 2, to control the temperature of the surface of the brake pad insulator. Rotor 44 rotates as illustrated by arrow D.

Figure 4:
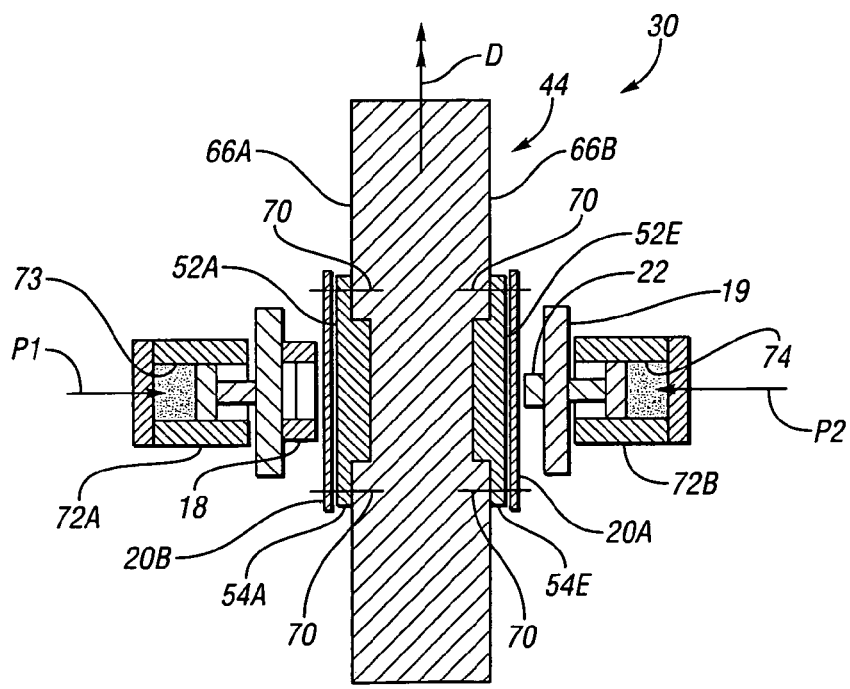
FIG. 4 is a cross-sectional illustration of the test apparatus taken at the arrows shown in FIG. 3.

Referring now to FIG. 4, a cross-sectional view of the test apparatus 30 taken at the arrow shown in FIG. 3 is illustrated. The rotor 44 has an inner surface 66A and an outer surface 66B. A first recess 52A is formed in the first outer surface 66A and a second recess 52E is formed in the second outer surface 66B. The carrier member 54A is supported at the recess 52A and the carrier member 54E is supported at the recess 52E. Carrier member 54A supports brake pad insulator material 20B (of FIG. 1) and carrier member 54E supports brake pad insulator material 20A (of FIG. 1). The rotor 44 is shown supporting the carrier member 54A and 54E and the insulator material 20A and 20B via attachment members 70 shown extending through the respective insulator materials 20A and 20B, carrier members 54A and 54E, and the rotor 44. The attachment members 70 may be bolts, screws or other fastening devices, preferably designed for removeability to change the insulator material 20A, 20B in performing multiple tests with the test apparatus 30. Alternatively, the insulator material 20A, 20B may be adhered or otherwise bonded to the carrier members 54A, 54E, respectively. Likewise the carrier members 54A, 54E may be adhered or otherwise fastened to the rotor 44 in lieu of using attachment members 70. Different brake material brake pad insulator types may be tested on recesses formed on the same outer surface of the rotor 44, such as recesses 52A-52D of FIG. 3 or the same brake pad insulator material may be tested. Additionally, the same or different brake pad insulator material types may be represented by brake pad insulator materials 20A and 20B of FIG. 4, but preferably 20A and 20B are of the same brake pad insulator material because the same type of insulator material will likely be in contact with both the piston 18 and the caliper finger 22 of FIG. 1 in any brake application.

A first actuator 72A (also shown in FIG. 3 being supported by the stator 46) supports the piston 18 (the same piston 18 as used on the brake assembly 10 of FIG. 1) and is pressurizable via fluid pressure (illustrated by arrow P1) in actuator chamber 73 controlled by the controller 49 on the dynamometer 32 of FIG. 2 to move the piston 18 into contact with the brake pad insulator material 20B. Likewise, a second actuator 72B supports a coupon (i.e., a sample) of the caliper finger 22 of FIG. 1 on piston 19 that is pressurizable via fluid pressure in actuator chamber 74. The fluid pressure is controlled by the controller 49 on the brake dynamometer 32 of FIG. 2 (and is indicated by arrow P2) to bring the caliper finger coupon 22 into contact with the brake pad insulator material 20A (contact not shown in FIG. 4). Surface friction of the brake pad insulator material 20A, 20B may then be determined based upon the measured torque, the axial force applied to the brake pad insulator material (which may be readily determined from the pressure applied by controller 49 of FIG. 2). Preferably, pressures P1 and P2 are controlled such that an equal amount of force is applied to the insulators 20A and 20B by the piston 18 and finger coupon 22, both in an axially-inward direction such that the forces cancel one another.

With reference to the structure of FIGS. 1-4, a method of measuring surface friction of a brake pad insulator material includes operatively connecting the brake pad insulator material 20A, 20B to a rotor 44 for rotation therewith. The method includes applying an axial force on the brake pad insulator material 20A, 20B (as illustrated by application of pressure P1 and P2, respectively in FIG. 4). The method further includes measuring the axial force, as by measuring the pressure P1 and P2 via controller 49 of FIG. 2. The pressure measured may then be easily converted by the controller 49 to an axial force based on the contact areas of the respective piston 18 and caliper finger 22. The method then includes powering the rotor 44 for rotation. Break-away torque of the rotor 44 is then measured via a torque cell 48. The calculation of surface friction of each sample of brake pad insulator material 20A and 20B may then be made based upon the measured axial force and torque. As discussed above with respect to the calculation of surface friction, it is also necessary to know the effective radius ($r_{eff}$) of the brake pad insulator material 20A, 20B at the point at which the force is applied. This may be measured from the axis of rotation (A in FIG. 3) to the effective center of contact of the respective piston 18 and finger 22 (illustrated schematically as R in FIG. 3).

If it is desired to correlate the brake pad insulator material surface friction with temperature, the method may include controlling the temperature of the brake pad insulator material. The temperature may be controlled by the heater element 60 and temperature element 62 illustrated in FIG. 3 or by controlling a temperature in the chamber or shed 33 of FIG. 2.

The method may also include creating a recess in the rotors such as recesses 52A and 52E in the rotor 44 shown in FIG. 4. Securing a carrier member at least partially within the recess for rotation with the rotor may be included in the method as shown by carrier members 54A and 54E in FIG. 4. Finally, connecting the brake pad insulator material (i.e., insulator material 20A and 20B in FIG. 4) to the carrier members 54E and 54A, respectively, may also be included.

Because the test apparatus 30 is designed to be used for multiple tests with different types of brake pad insulator material and or different samples of brake pad insulator materials, the method may also include removing the brake pad insulator material from the carrier member and connecting a second sample of brake pad insulator material to the carrier member. Thus, brake pad insulator materials 20A and 20B may be removed from the carrier members 54E and 54A, respectively and additional brake pad insulator material may be placed thereon for subsequent testing by repeating the application of the axial force, measuring the axially force, powering the rotor 44 and measuring torque of the rotor 44 to allow calculation of surface friction of the second sample of brake pad insulator material.

The test apparatus 30 employs the brake dynamometer 32 for test purposes. Accordingly, a method of using a brake dynamometer is presented. The method includes providing a rotor 44, a stator 46, one or more actuators 72A, 72B and a damping material (i.e., brake pad insulator material such as 20A or 20B of FIG. 4). The method of using a brake dynamometer further includes operatively connecting the rotor 44 with the rotatable shaft 36 of FIG. 2 of the dynamometer 32 for common rotation therewith. The method of using a brake dynamometer also includes grounding the stator 46. The method also includes operatively connecting the actuator (i.e., actuator 72A or 72B of FIG. 4), with the stator 46 and with the controller 49 of FIG. 2. The damping material 20A, 20B is then connected to the rotor 44, and under the method, force is applied to the damping material via fluid pressure applied to the actuators 72A and 72B via the controller 49. The method then includes rotating the rotor 44 while the force is being applied and measuring torque on the rotor 44 (by the torque cell 48), to allow calculation of surface friction of the damping material (i.e., the brake pad insulator material 20A, 20B).

The method of using a brake dynamometer may also include forming a recess in the rotor 44 such as recesses 54A and 54E of FIG. 4. The step of operatively connecting the damping material (i.e., the brake pad insulator material 20A, 20B) to the rotor 44 includes the step of supporting the carrier member 54A, 54E at least partially within the recess (i.e., 52A, 52E, respectively), and connecting the brake pad insulator material 20A, 20B to the respectively carrier member 54A, 54E.

As discussed above with respect to the test apparatus 30 and with respect to the method of measuring surface friction of brake pad insulator material, first and second samples of brake pad insulator material may be operatively connected to the respective outer surfaces 66A, 66B of the rotor 44 such that the applying force step includes applying the force to the first sample (i.e., brake pad insulator material 20B) via the actuator 72A and applying a force to the second sample (i.e., brake pad insulator material 20A) via the second actuator 72B. The applied forces are axially opposed so that no net axial force is applied to the rotor 44.

As described above, the method of using a brake dynamometer may include controlling the temperature of the brake pad insulator material to permit a correlation of the calculated surface friction with temperature. Finally, because the torque cell existing on a brake dynamometer (which is likely to be located in the same location as torque cell 48 of FIG. 2) may be calibrated to measure much higher torque loads, the method of using a brake dynamometer may include replacing the existing torque cell with the replacement torque cell 48.

While the best mode for carrying out the invention has been described in detail, those familiar with the art to which this invention relates will recognize various alternative designs and embodiments for practicing the invention within the scope of the appended claims.

The invention claimed is:

1. A test apparatus for measuring surface friction of damping material, comprising:
   a rotor configured to operatively support the damping material for rotation therewith, the rotor having an outer surface with a recess therein;
   at least one actuator operable to apply axially-inward force on the damping material;
   a stator configured to operatively support said at least one actuator;
   a torque cell operable for measuring torque of the rotor in relation to force applied to the damping material by the actuator, thereby allowing a calculation of surface friction of the damping material; and
   a carrier member configured to be supported at least partially within the recess by the rotor for common rotation with the rotor, wherein the carrier member is operable for supporting the damping material.

2. The test apparatus of claim 1, wherein the rotor has a first outer surface and a second outer surface opposing said first outer surface;
   wherein the damping material includes a first sample and a second sample;
   wherein said at least one actuator includes a first actuator and a second actuator;
   wherein said first sample is operatively supported at said first outer surface and said second sample is operatively supported at said second outer surface; and
   wherein said first actuator applies an axially-inward force on the first sample and said second actuator applies an opposing axially-inward force on the second sample.

3. The test apparatus of claim 2, wherein said first sample is a first type of material and said second sample is a second type of material.

4. The test apparatus of claim 1, wherein the damping material includes a first sample and a second sample supported at different locations on the rotor.

5. The test apparatus of claim 1, wherein the damping material includes a first sample and a second sample, wherein the recess is a first recess, wherein the carrier member is a first carrier member, wherein the first carrier member operatively supports the first sample, wherein the outer surface has a second recess therein, the second recess being spaced from the first recess, and further comprising:
   a second carrier member configured to be supported at least partially within the second recess by the rotor for common rotation with the rotor, wherein the second carrier member operatively supports the second sample.

6. The test apparatus of claim 1, further comprising:
   a heater element operatively associated with the damping material for varying the temperature thereof.

7. The test apparatus of claim 6, further comprising:
   a temperature sensor operatively connected with the damping material for sensing the temperature thereof.

8. The test apparatus of claim 1, wherein the damping material is brake pad insulator material, and wherein said at least one actuator includes a brake piston and a brake finger coupon.

9. A method of measuring surface friction of a brake pad insulator material comprising:
   operatively connecting a brake pad insulator material to a rotor for rotation therewith;
   applying an axial force on the brake pad insulator material;
   measuring the axial force;
   powering the rotor for rotation;
   creating a recess in the rotor;
   securing a carrier member at least partially within the recess for rotation with the rotor;
   connecting the brake pad insulator material to the carrier member; and
   measuring torque of the rotor, thereby allowing a calculation of surface friction of the brake pad insulator material based on the measured axial force and torque.

10. The method of claim 9, wherein the brake pad insulator material is characterized by a temperature, and further comprising:
   varying the temperature of the brake pad insulator material, thereby permitting correlation of calculated surface friction with temperature.

11. The method of claim 9, wherein the brake pad insulator material is a first sample, and farther comprising:
   removing the brake pad insulator material from the carrier member;
   connecting a second sample of brake pad insulator to the carrier member; and
   repeating the steps of applying an axial force, measuring the axial force, powering the rotor and measuring torque of the rotor, thereby allowing a calculation of surface friction of the second sample of brake pad insulator material.

12. A method of using a brake dynamometer having a controller and a rotatable shaft, comprising:
- providing a rotor, a stator, at least one actuator and a damping material;
- operatively connecting the rotor with the rotatable shaft for common rotation therewith;
- grounding the stator;
- operatively connecting said at least one actuator with the stator and with the controller;
- operatively connecting the damping material to the rotor;
- applying force to the damping material via said at least one actuator;
- rotating the rotor while said force is being applied;
- measuring torque on the rotor, thereby allowing a calculation of surface friction of the damping material; and
- forming a recess in the rotor;
- wherein said operatively connecting the damping material to the rotor includes supporting a carrier member at least partially within the recess and connecting the damping material with the carrier member.

13. The method of claim 12, wherein the rotor has a first outer surface and a second outer surface opposing the first outer surface, wherein the damping material includes a first sample and a second sample;
- wherein the operatively connecting the damping material to the rotor step includes operatively connecting the first sample at the first outer surface and operatively connecting the second sample at the second outer surface; and
- wherein the applying force to the damping material includes applying a force to the first sample and applying a substantially equal, axially opposed force to the second sample such that no net axial force is applied to the rotor.

14. The method of claim 12, further comprising:
- controlling the temperature of the damping material via the controller, thereby permitting a correlation of the calculation of surface friction with temperature.

\* \* \* \* \*